United States Patent [19]

Godfrey

[11] Patent Number: 4,684,528

[45] Date of Patent: Aug. 4, 1987

[54] FLAVOR OF ZINC SUPPLEMENTS FOR ORAL USE

[75] Inventor: John C. Godfrey, White Plains, N.Y.

[73] Assignee: Godfrey Science & Design, Inc., White Plains, N.Y.

[21] Appl. No.: 756,070

[22] Filed: Jun. 10, 1985

Related U.S. Application Data

[63] Continuation-in-part of Ser. No. 619,079, Jun. 11, 1984, abandoned.

[51] Int. Cl.$^4$ .................. A23L 1/304; A23L 1/305; A23G 3/00
[52] U.S. Cl. .................. 426/74; 426/660; 424/49; 424/54; 424/58; 514/494
[58] Field of Search .................. 426/74, 660; 424/49, 424/54, 58; 514/494

[56] References Cited

U.S. PATENT DOCUMENTS

| 1,765,867 | 6/1930 | Granger | 426/74 |
|---|---|---|---|
| 2,512,537 | 6/1950 | Zellers | 426/74 |
| 2,999,752 | 9/1961 | Webb | 426/74 |
| 3,341,414 | 9/1967 | Cherkas | 426/660 |
| 4,216,237 | 8/1980 | Smith | 426/74 |
| 4,220,667 | 9/1980 | Jakinovich | 426/96 |
| 4,339,432 | 7/1982 | Ritchey et al. | 424/54 |
| 4,425,325 | 1/1984 | Ritchey et al. | 424/54 |
| 4,503,070 | 3/1985 | Eby | 514/494 |

*Primary Examiner*—Jeanette Hunter
*Attorney, Agent, or Firm*—A. W. Breiner

[57] ABSTRACT

Formulations of zinc compounds with select amino acids such as glycine (aminoacetic acid) in a base material are described. The base material can be a sweetening agent such as a hard or soft candy base, a syrup, chewing gum, dentifrice, or the like. The advantage of such formulations is that the unpalatable and undesirable tastes and aftertastes of unformulated zinc compound and of zinc compounds mixed with a base material are markedly reduced and the products may be slowly dissolved in the mouth to achieve nutritional or therapeutic results. Processes for the satisfactory preparation of the formulations are set forth.

13 Claims, No Drawings

FLAVOR OF ZINC SUPPLEMENTS FOR ORAL USE

RELATED APPLICATION

This application is a continuation-in-part of U.S. application Ser. No. 619,079 filed June 11, 1984, now abandoned entitled "Improvements in the Flavor of Zinc Supplements For Oral Use."

FIELD OF INVENTION AND BACKGROUND

This invention relates to zinc supplements for oral use. More particularly, this invention relates to compositions containing a zinc compound which, when taken orally, is palatable without undesirable aftertaste. These compositions include, in addition to the zinc compound, a base material and a select amino acid.

The value of nutritional supplements of the element zinc is well established. Although zinc has been known to be essential for plant growth for more than a century, its essentiality for the normal growth of animals was reported in 1934 and for man in 1963. Hypogonadism in males, skin changes, poor appetite, and mental lethargy are but some of the observable effects related to zinc deficiency in man. Carbonic anhydrase was the first zinc metalloenzyme, discovered in the 1930's. Today, approximately 70 enzymes, many of them essential to human well being, have been found to contain zinc, and the evidence is strong that zinc is required for many (if not all) of these enzymes to express their activity. Several enzymes required for nucleic acid metabolism have been shown to require zinc. In this group are ribonucleic acid (RNA) and deoxyribonucleic acid (DNA) polymerases, deoxythymidine kinase, and reverse transcriptase. It has been shown experimentally that the activity of deoxythymidine kinase in rapidly regenerating connective tissue decreases as early as six days after animals are placed on a zinc-deficient diet. This metabolic defect resulting from nutritional zinc deficiency is an indication of the fundamental importance of zinc for cell division and protein synthesis.

Until recently, zinc deficiency in man was considered unlikely because of the widespread availability of zinc in nature. However, recent evidence suggests that nutritional zinc deficiency may be common among the people of many developing countries where they subsist on high cereal protein diets. Only recently has it been recognized that the phytate content of such diets severely restricts zinc availability, which translates nutritionally to markedly depressed zinc absorption in man under many practical circumstances. Marginal zinc deficiency may be widespread even in the United States because of self-imposed dietary restrictions, use of alcohol and cereal proteins, and the increasing use of refined foods which decrease the intake of trace elements. As meat is a major dietary source of zinc, vegetarians who consume cereals as a major source of protein may be in double jeopardy of zinc deficiency.

Therapeutically, zinc has a vital role in certain diseased or debilitated states. Zinc therapy is life saving in acrodermatitis enteropathica, a genetic disease caused by an autosomal recessive trait, which, although rare, had an extremely high mortality rate until it was discovered in 1973 that chronic administration or oral zinc salts was not only life saving but capable of lifetime control of the disease. Zinc supplementation markedly improves wound healing in zinc-deficient individuals. Zinc deficiency is an important feature of many cases of sickle cell anemia characterized by growth retardation and hypogonadism, and zinc appears to have a pharmacological antisickling effect. Zinc has also been shown to be beneficial in the relief of acute inflammatory conditions associated with rheumatoid arthritis.

The safety of zinc supplements in excess of the amounts found in a normal diet is well documented. Although excessive zinc produces toxic symptoms, such symptoms are rare. An acute dose of 2 g of zinc sulfate has been recommended as an emetic. Except for extremely large doses, zinc is non-toxic.

Until the present time, the more or less water-soluble zinc compounds such as the sulfate, chloride, acetate, gluconate, and the like, have been formulated as solid tablets or enclosed in gelatin capsules which are swallowed whole. Accordingly, the taste buds and other taste apparatus in the mouth and throat were not affected. These formulations generally dissolve in the gastric juice of the stomach and release zinc ion to be absorbed into the system via the stomach and intestines. It has only recently been found by a serendipitous observation of G. A. Eby, D. R. Davis, and W. W. Halcomb as reported in "Reduction in Duration of Common Colds by Zinc Gluconate Lozenges in a Double Blind Study," *Antimicrobial Agents & Chemotherapy*, 1984, 25(1), pp. 20–24; that when modest quantities of zinc are slowly ingested by mouth so that the interior surfaces of the mouth and throat are intermittently bathed in a solution of ionic zinc, both the time course and the severity of the symptoms of the common cold are remarkably altered in a favorable way. Their double blind clinical study in sixty-five humans has shown that allowing a tablet containing about 23 mg of elemental zinc, such as zinc gluconate, to slowly dissolve in the mouth once every two hours during 12 to 16 hours a day (the waking hours) reduced the duration of colds from 10.8 days in the untreated group to 3.9 days in the zinc-treated group; and at every time after about one day, the zinc-treated patients had a great reduction in cold symptoms compared to the patients who did not receive zinc. While the reported observations are highly significant both from the point of view of statistical validity and of the importance of these observations to public health, the authors stated repeatedly in their paper that the disagreeable taste of the zinc gluconate tablets was a serious problem. Many patients receiving zinc gluconate discontinued the treatment on the first day "due to objection to treatment." The authors stated that "the zinc gluconate lozenges [tablets] we used caused a unexpected unpalatability and distortion of taste in many subjects . . . " and mentioned "the somewhat bitter aftertaste which some people report for zinc gluconate." Furthermore, "unpalatable taste," "distortion of taste," and "mouth irritation" were common objections.

Accordingly, in order to take advantage of the important effect of zinc upon the common cold it is necessary to develop a formulation or formulations of pharmaceutically acceptable zinc salts which are palatable enough to be taken with the frequency necessary to suppress the symptoms of the common cold.

Another reason for developing zinc formulations having acceptable taste is to permit an increased oral dosage. Thus, it has been found that the ingestion of zinc as tablets or capsules which pass directly to the stomach before disintegrating is ineffective for providing a zinc supplement for certain applications, including the control of cold symptoms.

It has been found, however, that while minimal improvements in the taste of zinc gluconate, zinc acetate, zinc citrate, and the like salts can be achieved by physically mixing these salts with a candy or syrup base and adding a flavoring agent such as fruit flavor concentrate, the products so obtained retain the objectionable taste characteristics of the unformulated salts to an undesirable and unacceptable degree.

PRIMARY OBJECTS AND GENERAL DESCRIPTION OF INVENTION

Accordingly, it is a primary object of this invention to provide a zinc supplement for oral usage which is palatable and which does not have a disagreeable aftertaste.

It is another primary object of this invention to provide a zinc supplement for oral usage which permits a large oral dosage in simple and convenient form.

These primary and other objects of the invention will be apparent from the following general description and the detailed examples.

According to the present invention, it has been found that compositions containing a zinc compound, a base material such as a candy or syrup and certain amino acids in which the molecular ratio of amino acid to zinc is in the range of two to twenty are very pleasant to the taste and leave no undesirable aftertaste.

The amino acids which have been found useful for the purpose of this invention are glycine, L-alanine, D,L-alanine, L-2-aminobutyric acid, D,L-2-aminobutyric acid, L-valine, D,L-valine, L-isovaline, D,L-isovaline, L-leucine, D,L-leucine, D-isoleucine, D,L-isoleucine, L-lysine, and D,L-lysine. It has also been found that complexes between zinc and the named amino acids having the composition $Zn(aminoacid)_2$ are water-soluble and have very good flavors when formulated with an excess of the same amino acid, said excess being in the range of 2 to 20 moles of the said amino acid per mole of $Zn(aminoacid)_2$. It has further been found that certain other amino acids such as aspartic and glutamic acids are not useful for this purpose. Therefore, it has been found that it is not possible to predict which zinc and amino acid combination will have an acceptable taste unless it is prepared and tested.

The zinc compound which can be used in combination with the amino acids noted above can be in any of the forms commonly used such as the sulfate, chloride, acetate, gluconate, ascorbate, citrate, aspartate, picolinate, orotate and transferrin salts, as well as zinc oxide and complexes of divalent zinc with the amino acids. It has been found, however, because of compatibility with the amino acids and the like, that the gluconate, citrate and acetate salts are particularly preferred.

The base material which can be utilized as a carrier for the zinc compound and the select amino acid can be a sweetening agent such as a soft or hard candy base; a syrup such as corn syrup; a gum material including chewing gums, or any other form which permits the oral intake of the zinc compound and particularly where the composition is retained in the mouth for a substantial period of time to permit prolonged contact in the mouth with the zinc or provide a slow release of the zinc into the mouth. Preferably the base material is a hard or soft candy base optionally containing a flavoring agent such as a fruit flavor concentrate or a syrup such as a natural or artificially sweetened syrup.

The following examples will serve to illustrate, but not to limit, the present invention.

PREPARATION OF HARD CANDY STOCK

A mixture of 400 g of sucrose, 160 ml of white corn syrup, and 160 ml of deionized water was heated to 212° F. while stirring in a one-liter Teflon-lined aluminum pan. When a clear solution was obtained, the mixture was heated without further stirring at the maximum rate possible without boil-over until the temperature of the mixture reached 300° F. The pale straw-colored product was poured in a 4 mm layer onto a lightly greased heavy aluminum pan. On cooling to room temperature, the layer was fractured into convenient-sized pieces and stored in a sealed container. The yield was 522.9 g of product known in the art as "hard crack" caramel.

COMPOSITIONS WITH HARD CANDY AS BASE MATERIAL

Examples 1–7 which comprise a hard candy base contain from 1 to 5.1 mg zinc per gram of the composition.

EXAMPLE 1

Lemon-Flavored Zinc Gluconate Formulation 70 g of hard candy stock was placed in a stainless steel (SS) pan and heated, while stirring, to just thoroughly melt the stock. To this hot stock was added 5.40 g of a dry, finely ground mixture containing 2.48 g of zinc gluconate, $Zn(C_6H_{11}O_7)_2.3H_2O$, and 2.92 g of anhydrous glycine, $C_2H_5NO_2$. The dry component was evenly distributed in the melted stock by thorough mixing; and, while the resulting mixture was still hot, 1.0 ml of lemon-flavored concentrate was added and stirred in. The still hot mixture was distributed among 24 lightly greased steel candy molds. The yield was 24 circular lozenges, average weight 2.6 g. The zinc content was 4.2 mg per gram, or 10.9 mg per 2.6 g lozenge.

A similar product containing no glycine had an unpleasant flavor and aftertaste.

EXAMPLE 2

Lemon-Flavored Zinc Acetate Formulation 70 g of hard candy stock was placed in a small SS pan and heated, while stirring, to just thoroughly melt the stock. To this hot stock was added 5.70 g of a dry, finely ground mixture containing 1.30 g of zinc acetate, $Zn(C_2H_3O_2)_2.H_2O$, and 4.40 g of anhydrous glycine, $C_2H_5NO_2$. The dry component was evenly distributed into the melted stock by thorough mixing; and, while still hot, 1.0 ml of lemon-flavored concentrate was added and stirred in. The still hot mixture was distributed among 24 lightly greased candy molds. The yield was 24 circular lozenges, average weight 2.7 g. The zinc content of the product was 5.1 mg/g, or 13.8 mg per 2.7 g lozenge.

A similar product containing no glycine had a sharp, undesirable taste and an unpleasant aftertaste.

EXAMPLE 3

Lemon-Flavored Zinc Citrate Formulations (a) Product Having 10.0 mg of Zinc per Gram 20 g of hard candy stock was placed in a small SS pan and heated, while stirring, to just thoroughly melt the stock. To this hot stock was added 3.20 g of a finely ground mixture of zinc citrate containing $Zn_3(C_6H_5O_7)_2 \cdot 2H_2O$ 0.73 g and anhydrous glycine 2.47 g. The dry component was distributed into the melted stock by thorough mixing; and, while the resulting mixture was still hot, 0.25 ml of lemon-flavored concentrate was added and stirred in. The final mixture was cooled in the pan and then fractured into convenient-sized chunks.

(b) Product Having 1.0 mg of Zinc per Gram

The same procedure was used to combine 20.0 g of hard candy stock, 225 mg of the same zinc citrate plus glycine mixture, and 0.25 ml of lemon-flavored concentrate.

(c) Product Having 2.5 mg of Zinc per Gram

The same procedure was used to combine 20.8 g of hard candy stock, 730 mg of the same dry zinc citrate plus glycine mixture, and 0.25 ml of lemon-flavored concentrate.

Similar products prepared without glycine had sharp, unpleasant flavors.

EXAMPLE 4

Lemon Flavored Zinc Glycine Complex Formulations (a) Preparation of Zinc Glycine Complex A mixture of 4.0690 g, 0.0500 mole, of ultra-pure zinc oxide (ZnO), and 8.2577 g, 0.1100 mole, of anhydrous glycine was heated to 190° F. in 75 ml of deionized water for 30 minutes in a boiling water bath. Only a small amount of white substance remained insoluble. The solution was gravity filtered while hot the filter was washed with 5 ml of hot water, and the filtrate was chilled to 32° F. The resulting crystalline precipitate was filtered off, washed with 60 ml of 91% isopropyl alcohol, and air dried for 12 hours at 150° F. The yield was 6.805 g.

Anal. calc'd for $C_4H_8N_2O_4Zn \cdot 1\frac{1}{2}H_2O$: ZnO, 33.83%. Anal. found: ZnO, 33.51%.

The complex between zinc and glycine is a known compound as described in "Glycinate Complexes of Zinc and Cadmium," B. W. Low, F. K. Hirshfield and F. M. Richards, *J. Am. Chem. Soc.*, 1959, 81, pp. 4412–4416; J. V. Dubsky and A. Rabas, Spisy Vidavny Prevodovedeclsou Fakultou Masarykovy Univ., No. 123, 3–18 (1930), *Chem. Abstr.*, 1932; 25, p. 26557; and "Complex Formation Between Metallic Cations and Proteins, Peptides, and Amino Acids," F. R. N. Gurd and P. E. Wilcox, *Adv. in Protein Chem.*, 1956, 11, pp. 311–418.

(b) Lemon-Flavored Product Preparation 22.5 g of hard candy stock was placed in a small SS pan and heated, while stirring, to just thoroughly melt the stock. Exactly 400 mg of the $Zn(glycine)_2 \cdot 1\frac{1}{2}H_2O$ complex prepared above was ground fine and added to the hot stock. It was evenly distributed into the melted stock by thorough mixing; and, while the mixture was still hot, 0.25 ml of lemon-flavored concentrate was added and stirred in. The resulting mixture was cooled in the pan and then fractured into convenient-sized chunks. The zinc content was 4.7 mg per gram of product.

(c) Preparation of Lemon-Flavored Product with Added Glycine

The same procedure was used to combine 22.8 g of hard candy stock, 402 mg of $Zn(glycine)_2 \cdot 1\frac{1}{2}H_2O$, and 1.309 g of glycine. The resulting product had 4.5 mg of zinc per gram.

EXAMPLE 5

Lemon-Flavored Zinc Alanine Complex Formulations (a) Preparation of Zinc Alanine Complex A mixture of 4.0690 g, 0.0500 mole, of ultra-pure zinc oxide (ZnO), and 8.909 g, 0.1000 mole, of anhydrous D,L-alanine was heated to 190° F. in 75 ml of deionized water for 20 minutes in a boiling water bath. An appreciable amount of substance remained insoluble. The mixture was filtered hot, and the clear filtrate was diluted to a total volume of 170 ml with 91% isopropyl alcohol. On cooling to 25° F., a crystalline product was formed. It was filtered off and dried at 150° F. for 12 hours, yield 4.897 g.

Anal. calc'd for $C_6H_{12}N_2O_4Zn \cdot \frac{1}{2}H_2O$: ZnO, 32.48%. Anal. found: ZnO, 32.60%.

The complex between zinc and D,L-alanine is a known compound as "Chemotherapeutic Drugs Against Viruses. XXXIV. Antiviral Effect of Zinc Complexes on Japanese B Encephalitis Virus," S. Akihama and S. Toyoshima, *Chem. Pharm. Bull.* (Tokyo), 1962, 10, pp. 1254–1257; and "Chelation of Some Bivalent Metal Ions with Alanine and Phenylalanine," V. Simeon and A. O. Weber, *Croat. Chem. Acta*, 1966, 38, pp. 161–167.

(b) Lemon-Flavored Product Preparation 20.5 g of hard candy stock was placed in a small SS pan and heated, while stirring, to just thoroughly melt the stock. Exactly 408 mg of the $Zn(D,L-alanine)_2 \cdot \frac{1}{2}H_2O$ complex prepared above was finely ground and added to the hot stock. It was evenly distributed into the melted stock by thorough mixing; and, while the resulting mixture was still hot, 0.25 ml of lemon-flavored concentrate was added and stirred in. The final mixture was cooled in the pan and fractured into small chunks. The zinc content was 5.1 mg per gram of product.

(c) Preparation of Product with Added Alanine

The same procedure was used to combine 21.6 g of hard candy stock, 414 mg of $Zn(D,L-alanine)_2 \cdot \frac{1}{2}H_2O$, and 1.472 g of anhydrous D,L-alanine. The resulting product had 4.6 mg of zinc per gram.

EXAMPLE 6

Lemon-Flavored Zinc L-Leucine Formulations (a) Preparation of Zinc L-Leucine Complex Anhydrous L-leucine, 5.2472 g, 0.0400 mole, was dissolved in 30 ml of deionized water and heated to 120° F. Ultra-pure zinc acetate dihydrate, $Zn(C_2H_3O_2)_2 \cdot 2H_2O$, 4.3900 g, 0.0200 mole, was added in small increments over one hour, with stirring. The solution did not clear, so another 20 ml of water was added and the mixture was heated in a boiling water bath to 190° F. for an additional 2½ hours. Water was then added to a total volume of 75 ml, the mixture heated again to 190° F., and gravity filtered. The retained solid was dried at 150° F. for 12 hours, found to weigh 2.717 g, and was analyzed.

Anal. calc'd for $C_{12}H_{24}N_2O_4Zn \cdot H_2O$: ZnO, 24.98%. Anal. found: ZnO, 25.46%.

The clear filtrate from this first product was diluted to 300 ml with 91% isopropyl alcohol. The resulting precipitate of white flakes was filtered off and dried. Before drying, a few of the flakes were found to be immediately soluble in a few drops of water. After drying at 150° F. for 12 hours the product, 1.1216 g, was no longer freely soluble in water.

Anal. calc'd for $C_{12}H_{24}N_2O_4Zn$: ZnO, 26.45%. Anal. found: ZnO, 26.51%.

The complex between zinc and L-leucine is a known compound as described in "Chemotherapeutic Drugs Against Viruses. XXXIV. Antiviral Effect of Zinc Complexes on Japanese B Encephalitis Virus," S. Akihama and S. Toyoshima, *Chem. Pharm. Bull.* (Tokyo), 1962; 10, pp. 1254–1257.

(b) Lemon-Flavored Product Preparation 20.5 g of hard candy stock was placed in a small SS pan and heated, while stirring, to just thoroughly melt the stock. To this was added the finely ground anhydrous Zn(L-leucine)$_2$ complex prepared above, 398 mg, and 0.25 ml of lemon-flavored concentrate. The components were thoroughly distributed throughout the hot melt by stirring. The product was cooled in the pan and fractured into small pieces. The zinc content was 5.0 mg per gram of product.

(c) Preparation of Product with Added Glycine

The same procedure was used to combine 21.6 g of hard candy stock, 417 mg of Zn(L-leucine)$_2$, and 1.350 g of glycine. The resulting product had a zinc content of 4.7 mg per gram.

EXAMPLE 7

Lemon-Flavored Zinc D,L-Lysine Complex Formulations (a) Preparation of Zinc D,L-Lysine Complex A mixture of 2.035 g, 0.025 mole, of ultra-pure ZnO, 7.310 g, 0.050 mole, of anhydrous D,L-lysine, and 25 ml of deionized water was heated and stirred at 190° F. for 20 minutes. The cloudy solution was gravity filtered while hot, and the filter was rinsed with another 20 ml of hot water. No indication of a precipitate appeared when the clear filtrate was cooled to 85° F., so 225 ml of 91% isopropyl alcohol was added. A layer of oil settled to the bottom of the beaker. On cooling at 25° F. overnight, the oil crystallized. The white solid was filtered off and dried at 150° F. for 12 hours; yield, 6.80 g.

Anal. calc'd for $C_{12}H_{26}N_4O_4Zn.4H_2O$: ZnO, 19.02%. Anal. found: ZnO, 19.15%.

The complex of zinc with D,L-lysine is a known compound as described in "Chemotherapeutic Drugs Against Viruses. XXXIV. Antiviral Effect of Zinc Complexes on Japanese B Encephalitis Virus," S. Akihama and S. Toyoshima, *Chem. Pharm. Bull.* (Tokyo), 1962; 10, pp. 1254–1257.

(b) Lemon-Flavored Product Preparation 20.1 g of hard candy stock was placed in a small SS pan and heated, while stirring, to just thoroughly melt the stock. A quantity of 531 mg of the above Zn(D,L-lysine)$_2$.4H$_2$O complex was finely ground and added to the hot stock. It was evenly distributed into the melted stock by thorough mixing; and, while the resulting mixture was still hot, 0.25 ml of lemon-flavored concentrate was added and stirred in. The final mixture was cooled in the pan and fractured into convenient-sized chunks. The zinc content was 4.9 mg per gram of product.

(c) Preparation of Product with Added Glycine

The same procedure was used to combine 20.1 g of hard candy stock, 582 mg of Zn(D,L-lysine)$_2$.4H$_2$O, and 1.41 g of glycine. The resulting product had 5.0 mg of zinc per gram.

Similar formulations having good to excellent palatability are prepared from the zinc complexes of D,L-alpha-aminobutyric acid, L-valine, D,L-valine, L-isoleucine, D,L-isoleucine, L-isovaline, D,L-isovaline, L-lysine, and L-alanine. Similar formulations prepared with the dibasic amino acid/zinc complexes of L-aspartic acid, D,L-aspartic acid (20), L-glutamic acid, and D,L-glutamic acid were found to be highly unpalatable and to leave undesirable and persistent aftertaste.

COMPOSITIONS WITH SYRUP AS BASE MATERIAL

EXAMPLE 8

Preparation of Natural Syrup Containing Zinc Gluconate and Glycine

Zinc gluconate trihydrate 8.9 g and glycine 13.2 g were dissolved in 80 ml of water at 60° C. To this solution was added 65.0 g of sucrose and 60.0 g of light KARO ™ syrup containing 75% carbohydrate. An additional 68 ml of water was added, and the solution was warmed to about 70° C. to clarify. On cooling to room temperature, 1.0 ml of raspberry-flavored concentrate and three drops of McCormick's red food coloring were added and thoroughly mixed in to give a clear, deep pink solution. The final volume of solution was 250 ml, and the zinc ion concentration was 4.6 mg per milliliter. A taste test showed that the flavor was distinct from, and much improved over that of a similar solution which contained all of the same components at the same concentrations, except that glycine was omitted. Nevertheless, the distinctive and objectionable flavor of zinc gluconate was still detectable. The solution was then heated at 93° C. to 98° C. for 30 minutes, and then cooled to room temperature. After this treatment, the flavor characteristic of zinc gluconate was no longer present.

EXAMPLE 9

Preparation of Natural Syrup Containing Zinc Gluconate and L-Valine

A solution of 4.3 g of zinc gluconate trihydrate and 4.0 g of L-valine was prepared by heating the crystalline solids in 96 ml of water for 20 minutes at 80° C. This solution was added to a tared volumetric beaker containing 85.5 g of light KARO ™ syrup (75% carbohydrate) and 66.5 g of sucrose. The resulting mixture was heated just to the boiling point, producing a crystal clear solution. The final weight of solution was 245 g, and its final volume after cooling to 23° C. was 200 ml. It was then flavored with 1.0 ml of Candy Crafter's ™ Strawberry Oil No. 25201 and colored with 5 drops of McCormick's red food coloring. The zinc concentration in this syrup was 2.8 mg per milliliter. Its flavor was very pleasant.

EXAMPLE 10

Preparation of Natural Syrup Containing Zinc Gluconate and D,L-Alanine

Zinc gluconate trihydrate 8.6 g and D,L-alanine 14.5 g were dissolved in 96 ml of water by heating to 75° C.

The resulting solution was added to a beaker containing 85.5 g of light KARO ™ syrup and 66.5 g of sucrose. This mixture was stirred while heating just to the boiling point, producing a clear solution. It was removed from the heat and allowed to cool slowly to room temperature, 23° C., clear solution. It was flavored with 1.0 ml of Wilton's Maple Candy flavor and colored with 4 drops of McCormick's yellow food coloring. The final volume of this solution was 204 ml, and the zinc concentration was 5.4 mg per milliliter. It had a good, sweet maple flavor and the astringency of the zinc, while apparent, was not strong or objectionable.

EXAMPLE 11

Preparation of Natural Syrup Containing Zinc Gluconate and L-Leucine

Zinc gluconate trihydrate 4.66 g and L-leucine 2.40 g were dissolved in 96 ml of water by heating to 100° C. The resulting solution was added to a beaker containing 85.5 g of light KARO ™ syrup and 66.5 g of sucrose. This mixture was stirred while heating just to the boiling point, producing a clear solution. It was removed from the heat and allowed to cool slowly to room temperature, 23° C., clear solution. It was flavored with 1.0 ml of artificial raspberry flavor and colored with 4 drops of McCormick's red food coloring. The final volume of this solution was 196 ml, and the zinc concentration was 3.0 mg per milliliter. It had a good, sweet raspberry flavor and the astringency of the zinc, while apparent, was not strong or objectionable.

EXAMPLE 12

Preparation of Natural Syrup Containing Zinc Gluconate and D,L-Lysine

Zinc gluconate trihydrate 12.47 g and D,L-lysine 36.0 g were dissolved in 96 ml of water by heating to 85° C. The resulting solution was added to a beaker containing 85.5 g of light KARO ™ syrup and 66.5 g of sucrose. This mixture was stirred while heating just to the boiling point, producing a clear solution. It was removed from the heat and allowed to cool slowly to room temperature, 23° C., clear solution. It was flavored with 1.2 ml of Candy Crafter's ™ Wild Cherry flavor concentrate No. 25211 and colored with 6 drops of McCormick's red food coloring. The final volume of this solution was 214 ml, and the zinc concentration was 7.5 mg per milliliter. It had a very good flavor, and the zinc was detectable more by its characteristic mouth-feel than by its flavor.

EXAMPLE 13

Preparation of Natural Syrup Containing Zinc Acetate and Glycine

Zinc acetate dihydrate 9.16 g and glycine 31.3 g was readily dissolved in 96 ml of cold water. The resulting solution was added to a beaker containing 85.5 g of light KARO ™ syrup and 66.5 g of sucrose. This mixture was stirred while heating just to the boiling point, producing a clear solution. It was removed from the heat and allowed to cool slowly to room temperature, 23° C., clear solution. It was flavored with 0.9 ml of Candy Crafter's ™ Spearmint Oil No. 25191. The final volume of this solution was 210 ml, and the zinc concentration was 13.0 mg per milliliter. The flavor was refreshing, slightly acidic, with a definite astringency.

EXAMPLE 14

Preparation of Natural Syrup Containing Zinc Lysinate and Glycine

Zinc lysinate tetrahydrate 14.97 g and glycine 8.39 g were dissolved in 96 ml of water by heating to 50° C. The resulting solution was added to a beaker containing 85.5 g of light KARO ™ syrup and 66.5 g of sucrose. This mixture was stirred while heating just to the boiling point, producing a clear solution. It was removed from the heat and allowed to cool slowly to room temperature, 23° C., clear solution. It was flavored with 1.0 ml of artificial raspberry flavor and colored with 4 drops of McCormick's red food coloring. The final volume of this solution was 208 ml, and the zinc concentration was 11.0 mg per milliliter. The flavor was very similar to that of the product of Example 8 above.

EXAMPLE 15

Preparation of Natural Syrup Containing Zinc Glycinate and Glycine

Zinc glycinate sesquihydrate 4.82 g and glycine 8.39 g were dissolved in 96 ml of cold water. The resulting solution was added to a beaker containing 85.5 g of light KARO ™ syrup and 66.5 g of sucrose. This mixture was stirred while heating just to the boiling point, producing a clear solution. It was removed from the heat and allowed to cool slowly to room temperature, 23° C., clear solution. It was flavored with 1.0 ml of "5 oranges" artificial flavor and colored with 3 drops of McCormick's yellow food coloring and one drop of McCormick's red food coloring. The final volume of this solution was 203 ml, and the zinc concentration was 6.0 mg per milliliter. The flavor of this syrup was very good, and the presence of zinc ion was barely perceptible.

EXAMPLE 16

Preparation of Artificially Sweetened Syrup Containing Zinc Gluconate and Glycine A guar gum solution was prepared by moistening 2.0 g of guar gum with 4.0 ml of 91% isopropyl alcohol and adding to it 210 ml of cold water with vigorous stirring. After stirring for 15 minutes, an opalescent, viscous solution was obtained. It was heated to boiling and 10 ml of distillate was collected, ensuring the removal of all of the alcohol. The zinc gluconate 31.18 g and glycine 45.93 g were added to this hot solution, which was maintained just below its boiling point while stirring, until all added solids dissolved and the solution returned to its opalescent appearance. The resulting solution was allowed to cool slowly to room temperature, 23° C., and 1.0 g of calcium cyclamate was added, stirring to dissolve. It was flavored with 1.0 ml of Candy Crafter's ™ Wild Cherry Oil No. 25211 and colored with 5 drops of McCormick's red food coloring. The final volume of this solution was 200 ml, and the zinc concentration was 20.0 mg per milliliter. The viscosity of the solution was about the same as that of the corn syrup plus sucrose syrups prepared above. The flavor was comparable to that of the product described in Example 8 above, but this product is very noticeably more astringent.

EXAMPLE 17

Preparation of Artificially Sweetened Syrup Containing Zinc Gluconate and Glycine A guar gum solution was prepared by moistening 2.0 g of guar gum with 4.0 ml of 91% isopropyl alcohol and adding to it 210 ml of cold water with vigorous stirring. After stirring for 15 minutes, an opalescent, viscous solution was obtained. It was heated to boiling and 10 ml of distillate was collected, ensuring the removal of all of the alcohol. The zinc gluconate 31.18 g and glycine 45.93 g were added to this hot solution, which was maintained just below its boiling point while stirring, until all added solids dissolved and the solution returned to its opalescent appearance. The resulting solution was allowed to cool slowly to room temperature, 23° C., and 0.25 g of aspartame was added, stirring to dissolve. It was flavored with 1.0 ml of Candy Crafter's TM Wild Cherry Oil No. 25211 and colored with 5 drops of Mc-Cormick's red food coloring. The final volume of this solution was 200 ml, and the zinc concentration was 20.0 mg per milliliter. The viscosity of the solution was about the same as that of the corn syrup plus sucrose syrups prepared above. The flavor was comparable to that of the product described in Example 8 above, but this product is very noticeably more astringent.

COMPOSITIONS WITH SOFT CANDY BASE MATERIAL

EXAMPLE 18

Preparation of Orange-Flavored Gum Drops Containing Zinc Gluconate and Glycine Gum drop candy was prepared by combining corn syrup, sucrose, corn starch, orange color, orange flavor, citric acid, and water; and boiling briefly to effect hydration of the corn starch. The resulting candy had the expected rubbery consistency when it had cooled to room temperature. A 67.8 g portion of this candy was cut into ½ cm cubes and placed in a pyrex baking dish with 8.6 ml of water and heated at 250° F. for one hour in an oven. The temperature of the oven was then raised to 300° F., and the baking dish was removed when the mixture began to bubble uniformly over its surface. At this point, 7.2 g of a finely ground mixture of zinc gluconate trihydrate 2.9 g and glycine 5.3 g was thoroughly blended with the semi-liquid candy base, and the final mixture was allowed to cool to room temperature. The weight of the product was 76.8 g and it contained 4.9 mg of zinc per gram. It was formed into 4.0 g pieces which were air dried at 100° F. for 22 hours, rolled in granulated sucrose, and wrapped in aluminum foil. The final product had a typical gum drop consistency and a pleasant orange flavor. The presence of zinc could be detected by its astringent mouth-feel, but there was no significant aftertaste.

EXAMPLE 19

Preparation of Lemon-Flavored Gum Drops Containing Zinc Gluconate and Glycine 79.0 g of lemon-flavored gum drop candy base was heated with 8.0 ml of water in a pyrex dish in an oven at 210° F. for one hour, and then at 250° F. for two hours. It was stirred to produce a smooth mass which was then blended with 8.3 g of a finely ground mixture containing 3.35 g of zinc gluconate trihydrate and 4.95 g of glycine. During the blending process, the mixture was given three five-second bursts of microwave energy in a microwave oven in order to maintain the temperature necessary to reduce the viscosity and produce a smooth product. The mixture was then dried at 105° F. in a circulating air oven for 18 hours, separated into 4 g pieces which were rolled in granulated sugar, and wrapped in aluminum foil. The concentration of zinc in this preparation was 4.7 mg per gram.

COMPOSITIONS WITH CHEWING GUM AS BASE MATERIAL

EXAMPLE 20

Preparation of Spearmint-Flavored Chewing Gum Containing Zinc Gluconate and Glycine 64.0 g of spearmint gum was heated in a pyrex bowl at 250° F. for 20 minutes and 6.8 g of finely ground mixture 2.75 g of zinc gluconate trihydrate and 4.05 g of glycine was blended into it with a stainless steel spoon. The mixture cooled rapidly, but its temperature was maintained by giving it two bursts of microwave energy totalling 35 seconds during the blending process. When it was thoroughly blended, the mixture was allowed to cool to about 105° F., and rolled into a ⅛-inch thick sheet which was then cut up into 4 g sticks of chewing gum. The zinc concentration in this product was 5 mg per gram, and the flavor and consistency were excellent. Zinc is slowly released upon chewing, as shown by the typical zinc mouth-feel, but the flavor remains pleasant and there is no unpleasant aftertaste.

COMPOSITIONS WITH TOOTHPASTE AS BASE MATERIAL

EXAMPLE 21

Preparation of Mint-Flavored Toothpaste Containing Zinc Gluconate and Glycine 38.3 g of a dentifrice containing sorbitol, water, hydrated silica, trisodium phosphate, sodium lauryl sulfate, di-sodium phosphate, xanthan gum, Carbomer-940 TM, sodium fluoride, sodium saccharin, titanium dioxide, spearmint oil, and FD&C Blue #1 was heated in a pyrex dish in an electric oven for 20 minutes at 250° F. To this hot dentifrice base was added 4.10 g of a finely ground mixture containing 1.66 g of zinc gluconate trihydrate and 2.44 g of glycine. The dry solid was thoroughly distributed in the hot mixture by vigorous stirring, and the temperature of the mixture was maintained during the distribution process by adding energy in the form of microwaves in an oven operating at 700 watts of power and 2450 megahertz (mHz). Microwave exposure was limited to three 5-second bursts. The final mixture was cooled to 100° F., and placed in a screw-capped toothpaste tube. When used in the normal manner to brush teeth, the product had a very pleasant mint flavor; and the presence of the zinc could not be detected by taste or by mouth-feel.

The zinc supplement compositions obtained according to the present invention which include the select amino acid possess in general very pleasant flavors. Although the characteristic flavor and mouth-feel of the zinc ion is present, it is markedly and unexpectedly modified by the presence of the select amino acids to the extent that the unpalatable taste, distortion of taste, and mouth irritation associated with, for example, unformulated zinc gluconate, are greatly reduced or eliminated. This permits the formulation of compositions which will release over an extended period of time substantial amounts of zinc ions locally in the mouth or in the mouth and throat as necessary for certain applications, including the control of the common cold. For example, a lozenge having a hard candy base will release approximately 23 mg of zinc uniformly over 20 minutes in an adult human having a normal amount of saliva produced under the stimulation of the hard candy. As will be apparent, the amount of zinc ion which will be released can be controlled by the amount of zinc compound incorporated into the base material. Also, as will be readily understood, if a rapid release of the zinc ion is desired, it may be more practical to use a soft candy or a syrup as the base material rather than a hard candy base. The present invention, therefore, provides the ability to release varying amounts of the zinc supplement over varying periods of time determined by the formulation and nature of the composition selected.

As will be apparent to one skilled in the art, various modifications can be made within the scope of the aforesaid description. Such modifications being within the ability of one skilled in the art form a part of the present invention and are embraced by the appended claims.

It is claimed:

1. A slow-release candy composition for oral consumption comprising a hard candy base material and uniformly contained in said hard candy base material a zinc compound and an amino acid, said amino acid being capable of forming a complex with said zinc compound and being capable of forming a complex with said zinc compound and being selected from the group consisting of glycine, L-alanine, D,L-alanine, L-2-aminobutyric acid, D,L-2-aminobutyric acid, L-valine, D,L-valine, L-isovaline, D,L-isovaline, L-leucine, D,L-leucine, D-isoleucine, D,L-isoleucine, L-lysine, and D,L-lysine; said composition containing from about 1 mg to about 5 mg of zinc for each gram of said composition, and the molar ratio of said amino acid to zinc being from about 2 to 20; whereby said zinc is slowly and uniformly released as said composition is being orally consumed.

2. The composition of matter of claim 1 wherein said amino acid is glycine.

3. The composition of matter of claim 1 wherein said zinc compound is a zinc salt in the form of a sulfate, chloride, acetate, gluconate, ascorbate, citrate, aspartate, picolinate, orotate and transferrin salt.

4. The composition of matter of claim 1 wherein said zinc compound is a complex of divalent zinc with said amino acid.

5. The composition of matter of claim 1 wherein the zinc compound is zinc gluconate.

6. The composition of matter of claim 1 wherein the zinc compound is zinc acetate.

7. The composition of matter of claim 1 wherein the zinc compound is citrate.

8. The composition of matter of claim 4 wherein said zinc complex is a zinc glycine complex having the formula $Zn(C_2H_4NO_2)_2 \cdot nH_2O$ in which n may have the values 1, 1½, or 2, combined with from 1.6 to 6.2 parts by weight of anhydrous glycine.

9. The composition of matter of claim 4 wherein said zinc complex is a zinc alanine complex having the formula $Zn(C_3H_6NO_2)_2 \cdot nH_2O$ in which n may have the values ½, 1, or 2, combined with from 1.8 to 7.1 parts by weight of the anhydrous amino acid alanine, having the formula $C_3H_7NO_2$.

10. The composition of matter of claim 4 wherein said zinc complex is a zinc D,L-lysine complex having the formula $Zn(C_6H_{13}N_2O_2)_2 \cdot 4H_2O$ combined with from 0.9 to 3.5 parts by weight of anhydrous glycine.

11. The composition of matter of claim 4 wherein said zinc complex is a zinc L-leucine complex having the formula $Zn(C_6H_{12}NO_2)_2$ and combined with from 1.1 to 4.6 arts by weight of anhydrous glycine.

12. The composition of matter of claim 4 wherein the zinc complex is zinc D,L-alpha-aminobutyric acid complex having the formula $Zn(C_4H_8NO_2)_2$, combined with from 1.4 to 5.6 parts by weight of anhydrous glycine.

13. The composition of matter of claim 4 wherein the zinc complex is zinc L-valine complex having the formula $Zn(C_5H_{10}NO_2)_2$, combined with from 1.2 to 5.0 parts by weight of anhydrous glycine.

* * * * *